United States Patent [19]

Brennan

[11] Patent Number: 5,003,059
[45] Date of Patent: Mar. 26, 1991

[54] DETERMINING DNA SEQUENCES BY MASS SPECTROMETRY

[75] Inventor: Thomas M. Brennan, Cupertino, Calif.

[73] Assignee: Genomyx, Inc., South San Francisco, Calif.

[21] Appl. No.: 209,247

[22] Filed: Jun. 20, 1988

[51] Int. Cl.$^5$ .................. C07H 21/00; C07H 21/04
[52] U.S. Cl. ........................... 536/27; 536/28; 536/29; 435/6; 935/77; 935/87
[58] Field of Search .................. 536/27-29; 435/6

[56] References Cited

U.S. PATENT DOCUMENTS 4,729,947  3/1988  Middendorf et al. .................. 435/6

FOREIGN PATENT DOCUMENTS 0157280 10/1985 European Pat. Off. .
0233053  8/1987 European Pat. Off. .
6111665  1/1986 Japan .

OTHER PUBLICATIONS

Sanger, "Determination of Nucleotide Sequences in DNA", *Science,* 214: 1205–1210 (1981).
Sanger, et al., *Proc. Nat. Acad. Sci.,* 74: 5463 (1977).
Ornstein et al., "Sequencing DNA Using $^{35}$S-Labeling: A Trouble-Shooting Guide", *BioTechniques,* 3, 476–483, (1985).
Smith, et al., *Nature,* 321, 674–679, (1986).
Prober, et al., "A System for Rapid DNA Sequencing with Fluorescent Chain-Terminating Dideoxynucleotides", *Science,* 238, 336–341, (1987).
Eckstein and Goody, "Synthesis and Properties of Diastereoisomers of Adenosine 5'-(O-1-Thiotriphosphate) and Adenosine 5'-(O-2-Thiotriphosphate)", *Biochemistry,* 15, 1685–1691, (1976).
Eckstein, "Phosphorothioate Analogues of Nucleotides", *Accounts of Chemical Research,* 12(6), 204–210, (1979).
Cohen, et al., "High Performance Capillary Electrophoretic Separation of Bases, Nucleotides and Oligonucleotides: Retention Manipulation via Micellar Solutions and Metal Additives", *Anal. Chem.,* 59: 1021–1027, (1987).
Smith, et al., "Capillary Zone Electrophoresis—Mass Spectrometry Using an Electrospray Ionization Interface", *Anal. Chem.,* 60: 436–441, (1988).
Sakairi et al., "Characteristics of a Liquid Chromatograph/Atmospheric Pressure Ionization Mass Spectrometer", *Anal. Chem.,* 60: 774–780, (1988).
Houk, R. S., "Mass Spectrometry of Inductively Coupled Plasmas", *Anal. Chem.,* 68: 97A–105A, (1986).

*Primary Examiner*—Ronald W. Griffin
*Assistant Examiner*—Gary L. Kunz
*Attorney, Agent, or Firm*—Allegretti & Witcoff

[57] ABSTRACT

This invention relates to the methods, apparatus, reagents and mixtures of reagents for sequencing natural or recombinant DNA and other polynucleotides. In particular, this invention relates to a method for sequencing polynucleotides based on mass spectrometry to determine which of the four bases (adenine, guanine, cytosine or thymine) is a component of the terminal nucleotide. In particular, the present invention relates to identifying the individual nucleotides by the mass of stable nuclide markers contained within either the dideoxynucleotides, the DNA primer, or the deoxynucleotide added to the primer. This invention is particularly useful in identifying specific DNA sequences in very small quantities in biological products produced by fermentation or other genetic engineering techniques. The invention is therefore useful in evaluating safety and other health concerns related to the presence of DNA in products resulting from genetic engineering techniques.

4 Claims, 2 Drawing Sheets

2A
FIG. 2
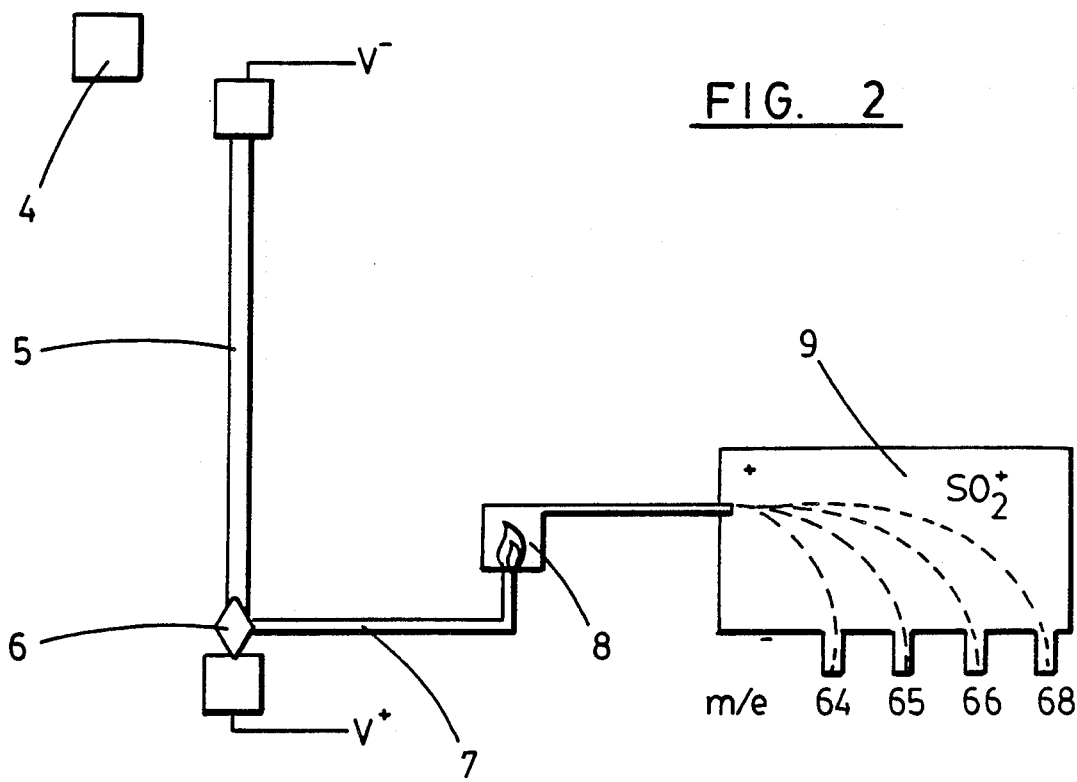
2B
DNA SEQUENCE    A C G T G T A C A C G T
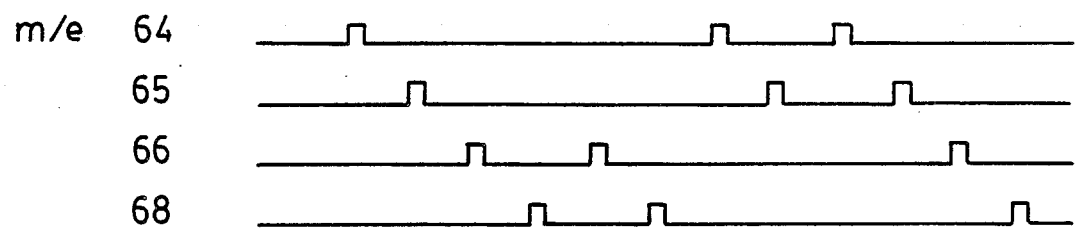
SO₂ ION CURRENT V. TIME

DETERMINING DNA SEQUENCES BY MASS SPECTROMETRY

BACKGROUND OF THE INVENTION

1. Field of the Invention

This invention relates to the field of the determination of DNA sequences and the uses of automated techniques for such determinations.

The ability to sequence DNA has become a core technology in molecular biology, and is one of the great achievements of the last decade. The ease with which sequencing may be accomplished will substantially affect the rate of development of new drugs produced by recombinant technology, the creation of new biosynthetic pathways and the promise of genetic engineering through manipulation of microorganisms, plants and mammalian cells, and the better understanding of a wide range of disease processes.

Initially, researchers focused on reading the genetic code and the translation of the nucleotide sequence into protein amino acid sequence. This occurs by a process of DNA transcription into mRNA, and then actual synthesis of the protein on ribosomes. In eucarotic cells, large specific segments of mRNA, introns, may be excised during an intermediary processing step. Much of the chromosomal DNA is not translated, and its specific function is largely unknown. This "excess" DNA was first thought to be excess genetic material. However, as biologists begin to unravel the details of cell differentiation and the processes controlling gene transcription it is now felt that the specific sequence of these large portions of untranslated DNA may also provide important regulatory signals.

The potential applications which derive from DNA sequencing have only begun to be explored. On large scale, analysis of human chromosomal DNA is considered vital to understanding genetic diseases, AIDS and cancer because only subtle differences exist between normal DNA and DNA involved in pathological conditions. Serious consideration is now being given to the sequencing of the entire human genome—approximately 3 billion base pairs. The success of this project will depend on rapid, sensitive, inexpensive automated methods to sequence DNA.

The fundamental approach to determination of DNA sequence has been well established. Restriction endonucleases are employed cleave chromosomal DNA into smaller segments, and recombinant cloning techniques are then used to purify and generate analyzable quantities of DNA. The specific sequence of each segment can then be determined by either the Maxam-Gilbert chemical cleavage, or preferably, the Sanger dideoxy terminated enzymatic method. In either case, a set of all possible fragments ending in a specific base are generated. The individual fragments can be resolved electrophoretically by increasing molecular weight, and the sequence on the original DNA segment is then derived by knowing the identity of the terminal base in each fragment.

In its broadest aspect, this invention is directed to methods and reagents for sequencing DNA and other polynucleotides. In particular, this invention described reagents and methods for automating and increasing the sensitivity of both the Sanger and Gish and Eckstein procedures for sequencing polynucleotides. The methods of the present invention are based on mass spectrometric determination of the four component terminal nucleotide residues, where the information regarding the identity of the individual nucleotides is contained in the mass of stable nuclide markers.

B. Summary Of The Prior Art

In the Sanger dideoxy method (Proc. Nat. Acad. Sci., 74, 5463 (1977)), the DNA to be sequenced is exposed to a DNA polymerase, a cDNA primer, and a mixture of the four component deoxynucleotides, plus one of the four possible 2,3-dideoxy nucleotides. There is a competition for incorporation of the normal deoxy- and the dideoxy- nucleotide by the polymerase into the growing complementary chain. When a dideoxy nucleotide is incorporated, further chain extension is prevented. Since there is a finite probability that this chain terminating event may occur at each complementary site of the appropriate base, a mixture of all possible fragments ending in that dideoxy base will be generated. This mixture of fragments can be separated by size on gel electrophoresis. When the experiment is repeated with each dideoxy base, four mixtures of fragments, each terminating in a specific residue are produced. When this set of mixtures is chromatographed in four adjacent lanes, so that fragment lengths in the four mixtures can be correlated with each other, the sequence of the original DNA is determined by relating the fragment length to the identity of the terminating dideoxy base.

The position of the fragment in gel electrophoresis is usually revealed by staining or by autoradiography. In autoradiography methods, the fragments have typically been labeled with $^{32}P$ or $^{35}S$ radionuclides where either the DNA primer or one of the component deoxynucleotides have been tagged, and that label incorporated in a specific or random fashion. The potential number of residues which can be sequenced by this method is limited by the experimental ability to correlate the results of the four chromatograms (electrophoretograms).

An alternate method of detection was developed by the California Institute of Technology group (Smith, et al., Nature, 321, 674 (1986)) in which the identity of the terminal base residues is contained in a fluorescent marker attached to the DNA primer. If four fluorescent markers of different spectral emission maxima are used, then the four separate sets of polymerase fragments can be combined and co-chromatographed. This method is also disclosed in EPO Patent No. 87300998.9.

A second variation of the fluorescent tagging approach has recently been reported by the DuPont group (Science, 238, 335 (1987)) wherein a unique fluorescent moiety is attached directly to the dideoxy nucleotide. This may represent as improvement over the CalTech primer tagging approach in that a single polymerase experiment can now be run with a mixture of the four dideoxy terminating bases. However, one trade-off for this simplification is potential transcription errors by the polymerase, arising from mis-incorporation of the modified dideoxynucleotide base analogs.

These modified Sanger methods are an improvement over the original Sanger method in the extent to which DNA an be sequenced because the chromatographic ambiguities have been reduced. However, a number of limitations are associated with the use of fluorescent labels in these modified Sanger reactions. In particular, there are chromatographic differences among fragments arising from the unique mobilities of the different organic fluorescent markers. Moreover, there is an inability to distinguish individual fluorescent markers because of overlap in their spectral bandwidths. Finally, there is a low sensitivity of detection inherent in the extinction coefficients of the fluorescent markers.

All of the above variants of the Sanger method of sequencing have used slab gel electrophoresis to effect separation of the DNA fragments. The casting and loading of slab gels is a skilled but intrinsically manual operation. The only aspect of this process which has been automated with any success are those commercial devices which read the gel with some type of laser scanner/spectrophotometer.

Eckstein and Goody, *Biochemistry*, Vol. 15, No. 8, p. 1685 (1976), discloses a method of chemical synthesis for adenosine-5'-(O-1-thiotriphosphate) and adenosine-5'-(O-2-thiotriphosphate).

Eckstein, *Accounts Chem. Res.*, Vol. 12, p. 204, (1978), discloses a group of phosphorothioate analogs of nucleotides.

Maxam and Gilbert, *methods Enzym.*, 65:499–500 (1980), disclosed a method for DNA sequencing using chemical cleavage. In this method, each end of a nucleotide to be sequenced is labeled. This nucleotide sample is then broken preferentially at one of the nucleotides, under conditions favoring one break per strand. This procedure is then repeated for each of the other three nucleotides. The four samples are then run side by side on an electrophoretic gel. Autoradiography identifies the position of a particular nucleotide by the length of the fragments produced by cleavage at that particular nucleotide. This method suffers from the same drawbacks as the Sanger method by requiring long periods of autoradiography and restricting the length of fragments which can be sequenced.

Gish and Eckstein close an alternative method for sequencing DNA and RNA employing base specific chemical cleavage of phosphothioate analogs of the nucleotides which were incorporated in a cDNA sequence. *Science*, 240, 1520–1522 (1988).

Ornstein, et al., *Biotechniques*, Vol. 3, No. 6, p. 476 (1985), discloses the advantages of using $^{35}S$ nucleotides rather than $^{32}P$ labelling in sequencing DNA.

Japanese Patent No. 59-131,909 (1986), discloses a nucleic acid detection apparatus which detects nucleic acid fragments which are separated by electrophoretic techniques, liquid chromatography, or high speed gel filtration. Detection is achieved by utilizing nucleic acids into which S, Br, I, or Ag, Au, Pt, Os, Hg or similar metallic elements have been introduced. These elements are generally absent in the natural nucleic acids. Introduction of one of these elements into a nucleotide on a nucleic acid allows that nucleic acid or fragment thereof to be detected by means of atomic absorption, plasma emission or mass spectroscopy. However, this reference does not anticipate any application of the described methods or apparatus to the sequencing of DNA, such as by the Sanger method. Specifically, it does not teach that a plurality of specific isotopes may be used to identify the specific terminal nucleotide residues. Nor does it teach that by total combustion of DNA to oxides of carbon, hydrogen, nitrogen and phosphorus, the detection sensitivity by mass spectrometry for trace elements, such as sulfur which is not normally found in DNA, is vastly improved. The combustion step, which is one aspect of the present application, is essential to eliminate the myriad of fragment ions from DNA. These fragment ions would normally mask the presence of trace ions of $SO_2$ in conventional mass spectrometry.

What this reference does disclose is that DNA may be tagged (by undisclosed means) with trace elements, including sulfur, as an aid to detection of DNA, and that these trace elements may be detected by a variety of means, including mass spectrometry.

Details of DNA sequencing are found in *Current Protocol In Molecular Biology*, John Wiley & Son, Ny., N.Y. Edited by F. M. Ansubel, et al., 1978, Chapter 7 which is incorporated herein by reference. Smith, et al., *Anal. Chem.*, 1988, 60, 438–441, described capillary zone electrophoresis—mass spectrometry using an electrospray ionization interface and is incorporated herein by reference.

SUMMARY OF THE INVENTION

This invention relates to methods, apparatus, reagents and mixtures of reagents for sequencing DNA, DNA fragments, and other polynucleotides, whether naturally occurring or artifically made. In particular, this invention relates to a method for sequencing polynucleotides based on mass spectrometry to determine which of the four bases (adenine, guanine, cytosine or thymine) is a component of the terminal nucleotide. Specifically, the present invention relates to identifying the individual nucleotides in a DNA sequence by the mass of stable nuclide markers contained within either the dideoxynucleotides, the DNA primer, or the deoxynucleotides added to the primer. This invention is particularly useful in identifying specific DNA sequences in very small quantities in biological products produced by fermentation or other genetic engineering techniques. The invention is therefore useful in evaluating safety and other health concerns related to the presence of DNA in products resulting from genetic engineering techniques.

BRIEF DESCRIPTION OF THE FIGURES

FIG. 2A shows in combination a column for separating DNA sequences according o size and a means for sequentially transporting DNA sequences to a mass spectrometer.

FIG. 2B shows superimposed "ion current vs. time" printouts for $^{32}SO_2$, $^{33}SO_2$, $^{34}SO_2$, and $^{36}SO_2$ resulting from combustion of a chain terminated DNA sequence.

BRIEF DESCRIPTION OF THE INVENTION

Figure 1:
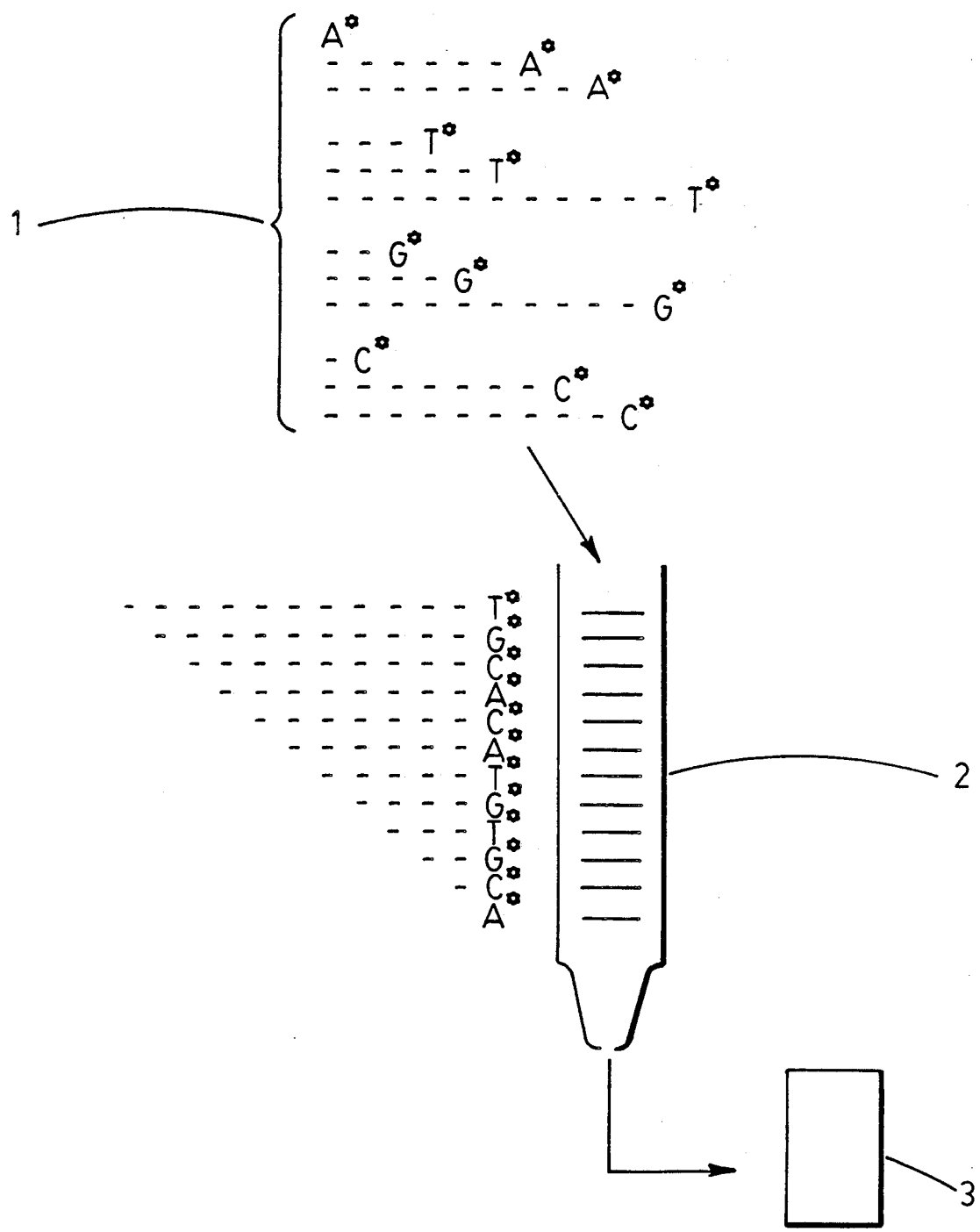
FIG. 1 shows a schematic diagram of a complementary DNA sequence attached to a primer DNA sequence and a typical series of chain terminated polynucleotide fragments prepared according to Scheme E herein.

This invention relates to methods, reagents, apparatus and intermediates involved in the determination of natural or artifically made ("recombinant") DNA sequences and fragments thereof. In particular, this invention involves the determination of DNA sequences using a combination of chain termination DNA sequencing techniques and mass spectroscopy. Thus, in a typical chain terminating DNA sequencing determination such as taught by Sanger, et al., *Proc. Nat. Acad. Sci.*, 74, 5463, (1977) involving a DNA primer, deoxynucleotidetriphosphates, dideoxynucleotidetriphosphates in the presence of a DNA polymerase, such as the Klenow fragment, are used to determine the DNA sequence. However, in embodiments of the present invention the DNA primer, the deoxynucleotides or the dideoxynucleotides are labeled with isotopes detectable by mass spectrometry to determine the DNA sequence.

For example, if the dideoxynucleotides (A, G, C, T) triphosphates, abbreviated as ddATP, ddGTP, ddCTP and ddTTP respectively, are labeled with isotopes of different masses respectively, and chain terminated fragments corresponding to those fragments are separated and analyzed by mass spectrometry, a direct reading of the DNA sequence is obtained. Generally, the labeled component of each dideoxynucleotide component of the chain terminated DNA sequence is converted to a more convenient species for mass spectrometry determination i.e. sulfur isotopes are oxidized to sulfur dioxide. If the DNa primer or deoxynucleotides are labeled, reactions between specifically labeled deoxynucleotides must be first carried out in the presence of a specific dideoxynucleotide. This is necessary so that a specific label is associated with a specific chain terminated DNA sequence. Once the individual reactions are conducted, the chain terminated DNa sequences can be mixed, separated, and analyzed by mass spectrometry because there will then be a specific relationship between a specific isotope and the terminal dideoxynucleotide. This invention is especially useful in determining the sequence of small quantities of DNA which are contaminants in products resulting from fermentation and other biotechnology related processes, i.e. "screening". The invention also includes reagents and analytical instruments for carrying out the above methods as well as intermediate mixtures of chain terminated DNA sequences produced while carrying out the methods of the present invention.

DETAILED DESCRIPTION OF THE INVENTION

This invention relates to an improved method for sequencing polynucleotides using mass spectrometry to determine which of the four bases (adenine, guanine, cytosine or thymine) is a component of the terminal nucleotide. In particular, the present invention relates to identifying the individual nucleotides in a DNA sequence by the mass of stable nuclide markers contained within either the dideoxynucleotides, the DNA primer, or the deoxynucleotides added to the primer. The invention also includes reagents and analytical instruments for carrying out the above methods as well as mixtures of chain terminated DNA sequences.

Information regarding the identity of the terminal base in a particular fragment may be signified by using a unique isotopic label for each of the four bases. The determination of which isotope marker, and thus which terminal base a fragment contains, can then be readily accomplished by mass spectral methods. Detection of ions by mass spectra is perhaps the most sensitive physical method available to the analytical chemist, and represents orders of magnitude better sensitivity than optical detection of fluorescence.

If stable isotopes are chosen for labeling, then the isotope ratios are fixed by the mode of synthesis. The group of suitable atomic ("nuclide") markers include those from carbon ($^{12}C$ / $^{13}/C$), chlorine ($^{35}Cl$ / $^{37}Cl$), bromine ($^{79}Br$ / $^{81}Br$) and sulphur ($^{32}S$ / $^{33}S$/ $^{34}S$ / $^{36}S$). Since sulfur, chlorine and bromine are not normal constituents of DNA, i.e. they are "foreign", analysis for those foreign isotopes does not require consideration of their natural abundance ratio. It is noted that sulphur is unique among this group in that is alone contains four stable isotopes, each of which can be used to represent one of the four nucleotide bases.

Further, if the fragments are subjected to combustion, then a light volatile derivative of the marker atom can be detected. Combustion converts DNA to the oxides of carbon, hydrogen, nitrogen and phosphorus. The inclusion of a combustion step enormously simplifies the detection of trace atoms because it eliminates the problems of producing and analyzing high mass molecular ions.

With sulphur, combustion of the polynucleotide fragments in a hydrogen-oxygen flame or pyrolysis tube will yield sulphur dioxide ($SO_2$). Thus, assignment of fragment terminal base identity reduces do determination of the mass of the $SO_2$ ion as 64, 65, 66, or 68. This is a simple distinction by existing mass spectral devices using either quadrupole or permanent magnet analyzers. For a permanent magnet device, a set of four permanently fixed ion detectors can be mounted to continuously monitor the individual ion currents. A quadrupole analyzer with a single ion-multiplier detector is presently preferred.

These are numerous ways in which a marker isotope could be incorporated into the complementary DNA fragment. These include substituting the marker isotope on the pyrimidine, purine, or ribose moieties, or the phosphate bridges between individual nucleotides. Further, the marker isotope may be contained in either part of the cDNA primer, randomly incorporated along the chain in one or several of the deoxy-base units, or specifically in the terminal dideoxy residue. The only restriction is that the particular substitution be unique for that particular set of fragments.

The site for the stable sulfur label is most preferably the phsophate bridge, using labeled thiophosphate in place of ordinary phsophate. The technique for inserting a stable thiophosphate label in place of ordinary phosphate is similar to that employed in conventional $^{35}S$ radiolabeling experiments. The chemistry and enzymology of the polymerase reaction using deoxynucleotide α-thiotriphosphates have been investigated extensively. Any future developments in cloning vectors or polymerase enzymes should also be able to utilize the thiosphosphate derivatives of the present invention.

If the isotope label is to be incorporated into the cDNA primer or randomly along the chain as a deoxybase surrogate, then it is necessary to perform a separate polymerase experiment with each of the appropriate dideoxy-base residues prior to mixing and chromatography. The advantage of using primer or intra-chain labeling is that several atoms of the marker isotope may be incorporated per mole of DNA fragment, and thus enhance detection sensitivity.

If, on the other hand, the isotope label is contained in the dideoxy base itself, then it is not necessary to perform individual polymerase experiments. Instead, a mixture of the four dideoxy bases, each with a unique isotope label, together with a mixture of the four normal deoxy bases in stoichiometric ratios appropriate for the specific polymerase enzyme could be used to generate the complete set of labeled fragments in a single polymerase experiment. Each fragment, regardless of its size, will contain one atom of the marker isotope on its terminal (dideoxy) nucleotide, wherein the marker isotope would indicate the identity of the terminal nucleotide.

Schemes A and B below illustrate typical sulfur and halogen labeling respectively, wherein an asterisk (*) is used herein to indicate the presence of an isotopic label in accordance with the present invention;

wherein by A, T, G, and C is meant the bases adenine, thymine, guanine, and cytosine respectively;

wherein by "Alk" is meant straight or branched chain lower alkyl of 1-6 carbon atoms;

wherein by "S*" is meant a sulfur isotope of the group of $^{32}S$, $^{33}S$, $^{34}S$ and $^{36}S$ with the proviso that each isotope be uniquely associated with a member of the group consisting of A, T, G, and C respectively; and wherein by "X*" is meant a "halogen" isotope of the group consisting of $^{35}Cl$, $^{37}Cl$, $^{79}Br$ and $^{81}Br$ with the proviso that each isotope be uniquely associated with a member of the group consisting of A, T, G and C respectively.

Scheme A
Sulfur Labeling
(a) at the phosphate bridge of "Rib":

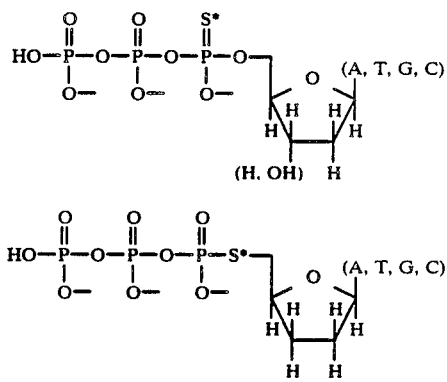

(b) on the deoxyribose:

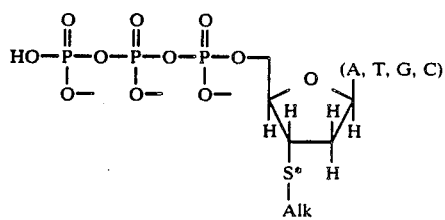

(c) on the base component:

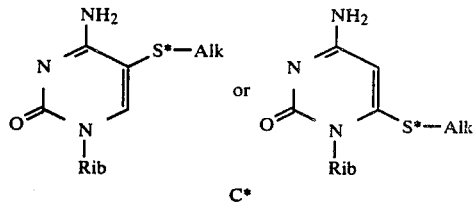

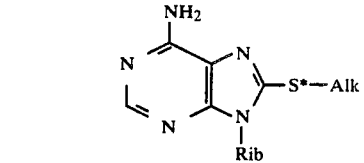

-continued
Scheme A

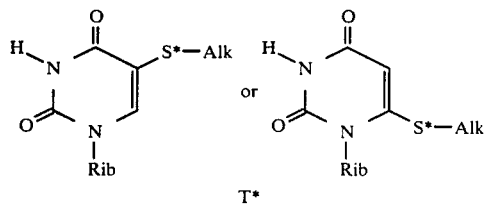

T*

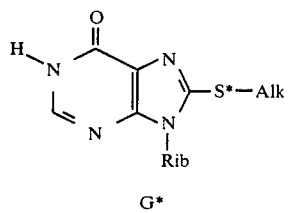

G*

Scheme B
Chlorine/Bromine Labeling
(a) On the deoxyribose

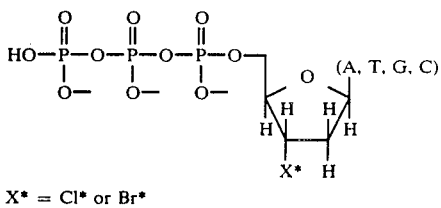

X* = Cl* or Br*

(b) On the base component

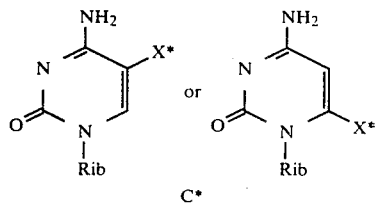

C*

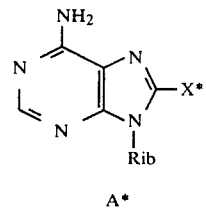

A*

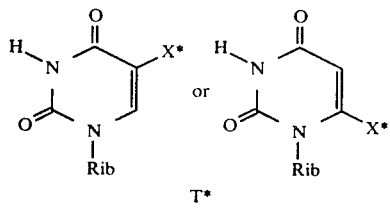

T*

-continued
Scheme B

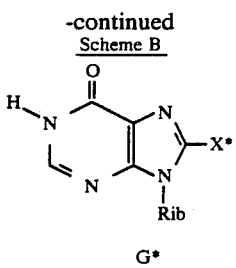

G*

Labeling Schemes C, D, and E below show three ways in which specific isotopes, designated as *1, *2, *3, and *4, can be uniquely associated with specific terminal nucleotides in a terminated complementary DNA (cDNA) sequence. For convenience in Schemes C-E, the "TP" designation for the deoxy and dideoxy triphosphates has been deleted. In the first two Schemes, (C and D), the dideoxy chain terminating reaction is conducted separately and then the terminated chains are mixed prior to separation. In particular, Scheme D is a modification of the chemical cleavage procedure of Gish and Eckstein, Science, 240, 1520 (1988) whereby the DNA fragment is selectively cleaved by base adjacent the phosphothioate linkage, leaving a labeled deoxy compound as the terminal nucleotide in the fragment. In Scheme D, one creates a series of such fragments which differ from one another solely in size, via the presence of an additional terminal nucleotide. Identification of each terminal nucleotide (via their isotopic marker) in relation to size of the fragment provides the base sequence of the DNA or polynucleotide of interest.

In Scheme E, a mixture of the four individually labeled dideoxy nucleotide triphosphates, together with a mixture of the four deoxy nucleotide triphosphates are reacted together with the primer ("P") in a single reaction. Because only one C Labeled Primers

| | | |
|---|---|---|
| 1. $P_{A*1}$ + d(A,C,G,T) + dd(A) | → | $P_{A*1}$dN_dN ... dd(A) |
| 2. $P_{C*2}$ + d(A,C,G,T) + dd(C) | → | $P_{C*2}$dN_dN ... dd(C) |
| 3. $P_{G*3}$ + d(A,C,G,T) + dd(G) | → | $P_{G*3}$dN_dN ... dd(G) |
| 4. $P_{T*4}$ + d(A,C,G,T) + dd(T) | → | $P_{T*4}$dN_dN ... dd(T) |

D. Labeled Deoxy

| | | |
|---|---|---|
| 1. P + d(A,C,G,T) + d(A*1) + dd(A) → | P ... dN_dA*1dN ... dd(A) |
| 2. P + d(A,C,G,T) + d(C*2) + dd(C) → | P ... dN_dC*2dN ... dd(C) |
| 3. P + d(A,C,G,T) + d(G*3) + dd(G) → | P ... dN_dG*3dN ... dd(G) |
| 4. P + d(A,C,G,T) + d(T*4) + dd(T) → | P ... dN_dT*4dN ... dd(T) |

E. Labeled Dideoxy

| | |
|---|---|
| 1. P + d(A,C,G,T) + dd(A*1,C*2,G*3,T*4) → | P ... dN_dN ... dd(A*1) |
| | P ... dN_dN ... dd(C*2) |
| | P ... dN_dN ... dd(G*3) |
| | P ... dN_dN ... dd(T*4) | reaction and one separation need be run in Scheme E, it can be readily seen that the labeled dideoxy scheme, Scheme E, is the preferred method of the present invention. Particularly preferred reactants in Scheme E are the labeled dd(A*,C*,G*, or T*) triphosphates where the labels $^{32}S$, $^{33}S$, $^{34}S$ and $^{36}S$ replace a phosphate oxygen as shown in Scheme A.

Accordingly, the invention not only includes reagents but also a mixture of unique isotopically labeled dideoxynucleotide triphosphates (ddC*TP, ddG*TP, ddT*TP and ddA*TP) where each dideoxynucleotide triphosphate is labeled with a different sulfur or halogen isotope. In particular, sulfur labeling, consisting of the isotopes $^{32}S$, $^{33}S$, $^{34}S$ and $^{36}S$, is preferred.

The invention also includes the intermediate mixture of dideoxy chain terminated DNA sequences where each chain terminated DNA sequence contains an isotope measurable by mass spectrometry which is related to a specific chain terminating dideoxynucleotide. Considering the dideoxynucleotide chain terminated DNA sequence to have the following sections: DNA primer—deoxynucleotide segment—chain terminating dideoxynucleotide, either section of the chain terminated DNA sequence can be labeled, provided the labeling procedure associates a specific label with a specific chain terminating dideoxynucleotide. The invention also includes the mixture of isotope labeled chain terminated DNA sequences separated by size.

Although this invention has been discussed in terms of sequencing DNA, there is no reason to believe that it could not also be used to sequence RNA by substituting a unique isotopically labeled uridine nucleotide triphosphate, UTP, in place of the deoxythymine nucleotide triposhpate d(T)TP, discussed herein.

FIG. 1 illustrates a complementary DNA sequence attached to a promoter DNA sequence and typical series of chain terminated polynucleotide fragments prepared according to Scheme E from mixtures of deoxynucleotide triphosphates and labeled dideoxy nucleotide triphosphates. These labeled fragments illustrate labeled chain terminated complementary DNA sequences 1 prepared by the method of the present invention, wherein the size of each complementary DNa fragment corresponds to the relative position of that fragment's terminal nucleotide in the overall complementary DNA sequence. These labeled fragments sequences are separated by size by an electrophoresis column 2. The fragments from the electrophoresis column 2 are sequentially eluted to a detector 3. FIG. 2A shows in more detail the apparatus for determining a DNA sequence. DNA sequences are prepared in reaction chamber 4. The mixture of labeled terminated DNA fragments are separated according to size by electrophoreses on a polyacrylamide gel column 5 wherein migration occurs from the cathode ($V^{31}$) to the anode ($V^{30}$). the fractions are taken off the polyacrylamide gel column 5 sequentially by size at transfer point 6 where there is provided a means 7 for transferring the terminated DNA fragments to an oxidizer or combustion chamber 8. In the oxidizer or combustion chamber 8, the sulfur label is oxidized to $SO_2$ and the labeled $SO_2$ is detected in a mass spectrometer 9. FIG. 2B shows typical superimposed "ion current v. time" plots for m/e 64, 65, 66, and 68, corresponding to ions produced by the four stable isotopes of sulfur, i.e., $^{32}SO_2$, $^{34}SO_2$, and $^{36}SO_2$, respectively. When the stable isotopes of sulfur associated with the bases, A, C, G and T are $^{32}S$, $^{33}S$, $^{34}S$, and $^{36}S$ respectively, a plot corresponding to the DNA sequence illustrated at the top of FIG. 2B is obtained. In this manner, the DNA sequence of any genetic material can be determined automatically and on femto- to nanomolar quantities of material.

There are several variations in the design of an automated DNA sequencer of the present invention. The major components of the device are the reaction chamber for conducting polymerase reactions, the chromatographic device consisting of some form of electrphoresis, the effluent transport, the combustion system, and the mass spectral analyzer. Because this instrument is designed to operate on nano- to femto-molar quantities of DNA, it is important that the geometry of all component systems be kept to a minimum size.

The chromatographic system may be of a laned plate or tubular configuration. In the plate designs, the supporting medium for the chromatogrpahic separation will be most preferably a polyacrylamide gel, where the ratio of acrylamide to bis-acrylamide is more preferably between 10:1 and 100:1. Although persulfate is the typical polymerization catalyst used by most workers, the background of sulfate ions may be unacceptably high without extensive washing. Sodium perborate or ultraviolet irradiation can be used successfully to initiate cross-linking and produce high quality gels, which can be used immediately without washing.

For tubular designs, the chromatographic separation may be conducted in a gel-filled capillary or in an open tubular configuration. The preferred dimensions of the capillary depend on whether an open or gel-filled medium is selected. For gel-filled devices, preferred diameters are 50 to 300 microns. In open tubular configurations, however, the preferred diameters are 1 to 50 microns. The preferred length of the capillary depends on the diameter and the amount of DNA sample which will be applied, as well as the field strength of the applied electrophoretic voltage. The preferred length is optimally between 0.25 and 5 meters.

For open tubular configurations, the capillary will preferably be fabricated from fused silica. Under typical operating conditions, where the pH of the buffer is usually maintained in a range of 5.0 to 11.0, the surface of the silica will have a net negative charge. This surface charge establishes conditions in which there is a bulk electroosmotic flow of buffer toward the negative electrode. The DNA fragments also possess a negative charge and are attracted to the positive electrode. Hence, they will therefore move more slowly than the bulk electroosmotic flow. In gel-filled devices, the supporting medium minimizes electroosmosis. Since the gel has no charge, the negatively charged DNA fragments migrate toward the positive electrode.

There are a variety of techniques to modify the surface charge on the wall of an open capillary. One particularly useful method is to covalently modify the wall with a monomer such as methacryloxypropyltrimethoxysilane. This monomer can then be crosslinked with the acrylamide to give a thin bonded monolayer which is similar in characteristics to the polyacrylamide gel-filled capillaries. The distinct advantage of the coated wall method is that the capillary can be recycled after each analysis run simply by flushing with fresh buffer. (See S. Hjerton, J. Chromatography, 347, 191, (1985) for details.)

The transfer system is selected to match the particular chrmoatographic design. The chromatographic system may be of laned plate or tubular configuration. It is desirable to have the chromatography effluent in a closed environment. The tubular configurations may be more amenable to sample transfer designs which pump, spray or aspirate the column effluate into the combustion chamber, and thus minimum degradation in resolution because of post-chromatographic remixing of fractions.

For the open plate type devices, a moving belt or wire system can be used satisfactorily. In this system, a thin coating of the column effluent is spread on the ribbon to transport the eluted fractions through a predrying oven and then into the combustion furnace. The transport ribbon may be fabricated from platinum or other nobel metal, and may be continuously looped because the ribbon can be effectively cleaned upon passage through the combustion furnace. Less preferably, the ribbon may be fabricated from a glass or ceramic fiber or carbon steel. In this design, the ribbon would be taken up on a drum for disposal.

For tubular configurations, the most preferred embodiment of the transfer system is to use an electrospray nebulizer method to create a fine aerosol of the column effluent. In this technique, a small charge of optimally less than 3000 volts is applied to the emerging droplet. The charge of a larger droplet tends to disperse it into a very fine mist of singly charged droplets. These fine charged droplets can be focused and directed by electric or magnetic fields, much as in an ink-jet printer head. It is important to control the temperature of the flowing gas stream into which the aerosol is introduced. If the temperature is too great, then the droplets will tend to evaporate on the capillary injector. If the temperature is too low to overcome the surface tension of the effluent, the individual droplets will not adequately be dispersed. The composition and ionic strength of the supporting electrolyte is important. The preferred buffers are phosphate or borate at less than 0.1 M concentration. Because the overall method is based on detection of trace atoms, it is critically important that the buffers be free of contaminant ions, such as sulfate.

A second satisfactory method to create an aerosol of the column effluent is an ultrasonic device which produces sufficient mechanical shear and local heating to disperse the droplet. A similar type of shear may also be generated off the tip of a capillary injector into a venturri type aspirator, where the flow of supporting gas is developed by the pressure differential into the mass spectrometer. In these designs, it is often desirable to add small amounts of additional aqueous or organic solvents at the tip in order to aid in the flash evaporation of the effluent.

The combustion section is designed to completely burn the vaporized or surface evaporated chromatography effluent of DNA fragments together with the supporting electrolytes and optional solvent modifier to the oxides of carbon, hydrogen, nitrogen, phosphorous, and most importantly, those of the marker isotope. The sensitivity of detection of the marker isotope is greatly affected by the efficiency of combustion, since low molecular weight fragment ions which may result from incomplete burning can mask the presence of the primary detection species. The specific mass/charge range which is must be free of interfering ions for sulfur dioxide detection is 64 to 68.

This combustion may be accomplished at moderate to approximately atmospheric pressure prior to injection into the mass spectrometer. For sulfur containing streams, essentially complete combustion to sulfur dioxide will be achieved when the sample is heated to temperatures in excess of approximately 1200° C. in an oxygen environment.

The most rugged design is to simply aspirate the column effluent into a hydrogen-oxygen flame, similar in design to standard gas chromatography flame ionization detectors. The important characteristics of the flame, the temperature and sample residence time, will be determined by the ratio of hydrogen to oxygen, the aggregate flow rate of gases and the local pressure. The characteristics of sulfur containing flames at 100–150 tor have been described by Zachariah and Smith, *Combustion and Flame*, 69, 125 (1987). A limitation to the sensitivity of this design is the volume of gas (water vapor) resulting from hydrogen-oxygen combustion which effectively dilutes the sulfur dioxide. Although the standard mass spectrometry techniques such as gas separators or semipermeable membranes may be used to remove water vapor, there is a trade-off between sample dilution and ultimate detectability which must be considered for each design.

A preferred method to very efficiently burn the nebulized column effluent is to inject it into a short heated tube in an oxygen environment. The tube may be constructed of nobel metals such as platinum, ceramic or quartz, depending on the method of heating. The external heating action may be provided by a cartridge electrical resistance heater or an external flame. The tube may be packed with a heat exchanger medium such as glass wool. Optionally, a catalytic surface may also be provided by such materials as supported platinum or copper oxide to enhance combustion efficiency.

A particularly effective method to burn the sample is in an inductively coupled oxygen plasma, where the tube forms the resonant cavity of a microwave generator. The inductively coupled plasma techniques have been reviewed by G. Meyer, *Anal. Chem.*, 59, 1345A (1987).

Alternatively, the combustion may be effected within the low pressure environment of the mass spectrometer. A standard ionization technique in mass spectrometry is fast atom bombardment. An energetic beam of atoms, usually xenon, is produced in a plasma torch and directed toward the sample. Ionization occurs by collision induced dissociation of this beam with the sample. If instead of pure xenon, oxygen is introduced into the fast atom beam, then both oxidation and ionization of the sample can occur. The limitation of this method however is the difficulty in achieving quantitative oxidation, and minimizing the background signal from incompletely oxidized low mass fragments.

There are several methods to effect ionization of sulfur dioxide. The objective is to obtain as high ion current as possible. In designs which operate at atmospheric pressure by flame, corona discharge needle or microwave induced plasma discharge, the ionization efficiency will be very high. In this type of design, a portion of the ionized gas in introduced into the low pressure region of the mass analyzer through a small sampling orifice or skimmer cone. The size of the orifice, and thus the percentage of total combustion sample which can be introduced, will depend on the pumping speed of the vacuum system. Generally, less than five percent of the sample will be transferred to the analyzer region. Designs of this type have been described by T. Covey, *Anal. Chem.*, 58, 1451A (1986) and by G. Hieftje, *Anal. Chem.*, 59, 1644 (1987).

Alternatively, the sample may be ionized in the lower pressure region near the analyzer. This may be achieved by such methods as electron impact using the beam emanating from a hot filament, by fast atom bombardment with inert gases such as xenon, or by chemical ionization with a variety of light gases. In these type of design, although the ionization efficiency is low relative to atmospheric methods, a greater percentage of those ions actually get to the analyzer section. The electron impact techniques have been described by A. Brandy, *Anal. Chem.*, 59, 1196, (1987).

An RF-only quadrupole mass filter may be used to help separate low molecular weight combustion products ($H_2O$, $N_2$ and $CO_2$).

The analyzer and ion detector sections can be selected from several commercially available designs. The analyzer may be a quadrupole device where mass selection depends on the trajectory in a hyperbolic field, a field swept electromagnetic device with a single ion detector, or a permanent magnet device with an array of four ion detectors tuned to the isotopes of interest. The detector may be of single stage or ion multiplier design, although the latter type is preferred for highest sensitivity.

When the mass spectrometer is being used to detect isotopes of sulfur dioxide, as would be the case when dideoxy terminated thiophosphates are being utilized, the highest sensitivity is achieved when the polarity of the spectrometer is set to determine the positive ion spectrum.

When the mass spectrometer is being used to detect isotopes of chlorine or bromine, then maximum sensitivity will be achieved when the spectrometer polarity is reversed, and the negative ion spectrum is detected.

The labeled compounds of the present invention are prepared by conventional reactions employing commercially available isotopes. For example, the sulfur isotopes: $^{32}S$, $^{33}S$, $^{34}S$ and $^{36}S$ are commercially available as $CS_2$ or $H_2S$ from the Department of Energy (Oak Ridge, Tenn. or Miamisburg, Ohio) at "isotopic enrichments" of 99.8%, 90.8%, 94.3% and 82.2% respectively. Although the method of the present invention will provide satisfactory results with the "isotopically enriched" commercial products, it is preferred that the sulfur isotopes be at 99.5% enrichment to facilitate interpretation of the ion current v. time plots.

Enrichment techniques for sulfur are well known in the art. In particular, $CS_2$ can be further enriched by fractional distillation which takes advantage of the different boiling points of $CS_2$ conferred by the various sulfur isotopes. Alternatively, gaseous diffusion of $SF_6$ also can provide further enrichment of the sulfur isotope of interest. Thereafter, the isotopically enriched $CS_2^*$, $H_2S^*$ or $SF^*_6$ are converted into the reagents described herein by techniques well known in the art.

The "halogen" isotopes $^{35}Cl$, $^{37}Cl$, $^{79}Br$, and $^{81}Br$ are also commercially available from the Department of Energy in either elemental form or as the corresponding halide salt at enrichments of 99%, 95%, 90% and 90% respectively. These isotopes are used herein in their commercially available form.

As shown in Scheme F, labeled 2',3'-dideoxynucleo-tide-5-(O-1-thiophosphates) III are prepared by initially reacting a 2',3'-dideoxynucleotide I with isotopically enriched thiophosphoryl chloride (PS*Cl$_3$) in triethyl phosphate, wherein by "S*" is meant a sulfur isotope that is a member of the group consisting of $^{32}S$, $^{33}S$, $^{34}S$ and $^{36}S$ in isotopically enriched form. From the above reaction, the correspondingly 2',3'-dideoxynucleotide-5'-(O-1-thiotriphosphate) III is prepared from II by dissolving the bistriethylamine (TEA) salt of II in dioxane and reacting it with diphenyl phosphochloriodate to form the diphenyl phosphate ester of II. This phosphate ester was further reacted with the tetrasodium salt of pyrophosphate in pyridine to form III. Purification of III is accomplished by chromatography on diethylaminoethyl (DEAE) cellulose.

Scheme G shows the general method for preparing 3'-halo-2',3'-dideoxynucleosides V wherein the halogen ("X*") is a member of the group consisting of $^{35}Cl$, $^{37}Cl$, $^{79}Br$, and $^{81}Br$ in isotopically enriched form. In particular, a solution of 1-(5-O-triphenylmethyl-2-deoxy-β-D-threopentofuranosyl)nucleoside wherein by nucleoside is meant A, T, G, or C, in a basic solvent, such as pyridine, was reacted with methanesulfonyl chloride. The resulting mesylate was treated with an isotopically enriched salt, such as LiX*, in the presence of heat and then acidified to produce a 3'-halo-2',3'-dideoxynucleoside V. Compounds of Formula V can be converted to the corresponding labeled nucleotide monophosphate VI by reaction with cyanoethyl phosphate and dicyclohexylcarbodiimide (DCC) followed by LiOH deblocking.

The corresponding triphosphate of V is prepared from the monophosphate as described from the monophosphate as described for the conversion of II to III above.

Scheme H present a method for halogenating a purine or pyrimidine base of a 2', 3'-dideoxynucleoside VII using isotopically enriched elemental bromine ($^{79}Br$ or $^{81}Br$) or chlorine ($^{35}cl$ or $^{37}Cl$), i.e. X$_2$*. The 2', 3'-dideoxynucleoside VII is dissolved in a polar solvent, such as dry DMF, in the presence of a base, such as pyridine. To the reaction mixture is added a molar equivalent of the elemental halogen (X$_2$*) and the reaction mixture is allowed to stir for 12 hours. Evaporation of the solvent produces the labeled 2',3'-dideoxynucleoside VIII wherein the isotopic halogen label is on the purine or pyrimidine base of the dideoxy nucleoside. Purification is accomplished by conventional chromatographic techniques.

The labeled 2',3'-dideoxynucleoside VIII is converted to the corresponding monophosphate and triphosphate as discussed above for VI and III respectively.

The examples described herein are intended to illustrate the present invention and not limit it in spirit or scope.

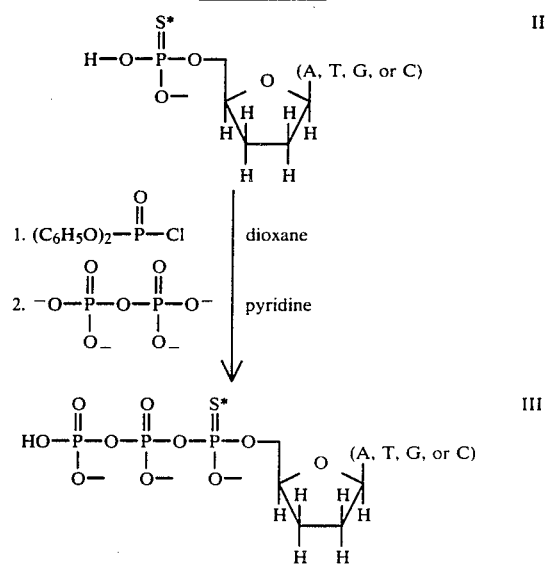

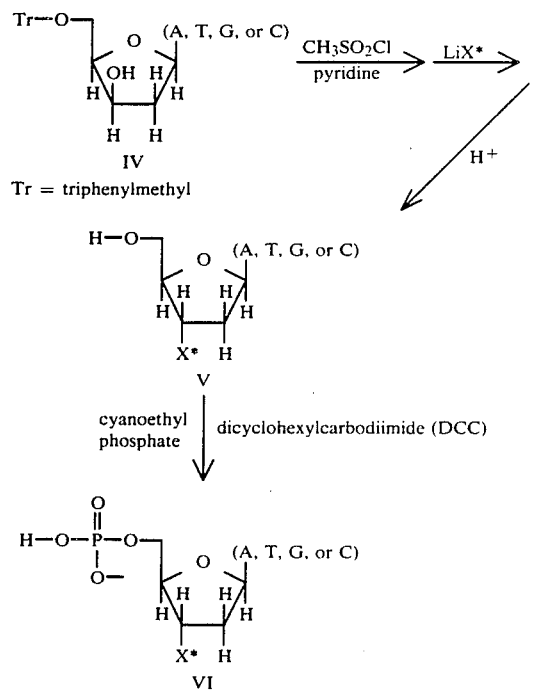

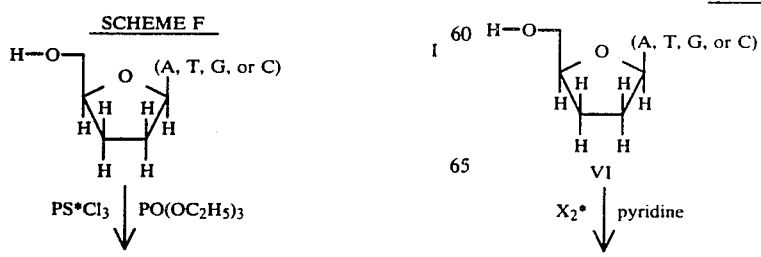

-continued
SCHEME H

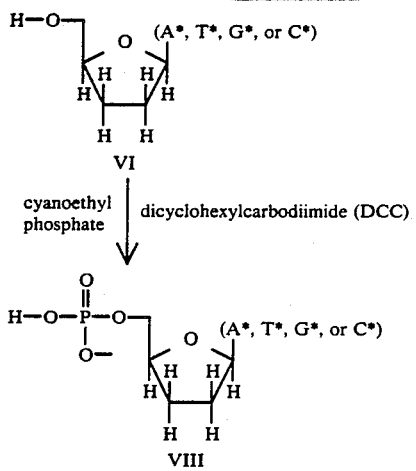

EXAMPLE 1

Preparation of [$^{32}$S]2',3'-Dideoxyadenosine-5'-Phosphorothioate

2',3'-Dideoxyadenoisine (47 mg, 0.2 mmol) was suspended in triethyl phosphate (0.5 ml) and heated briefly to 100° C. The solution was cooled to 4° C. and treated with [$^{32}$S] thiophosphoryl chloride (37 mg, 0.22 mmol). The mixture was agitated for 12 hr. at 4° C., and then treated with 2 ml 10% barium acetate and agitated at 20° C. for 1 hour. The suspension was treated with 0.5 ml triethyl amine and then with 5 ml 95% ethanol. The suspension was agitated 30 min. and then filtered. The precipitate was washed with 50% aqueous ethanol and then water. The filtrate was evaporated to dryness, and the solid taken up in water and chromatographed on a column of diethylaminoethyl (DEAE) cellulose which had been equilibrated with NH$_4$HCO$_3$. The column was eluted with 0.1 M NH$_4$HCO$_3$ and the fractions adsorbing at 260 nm were pooled and evaporated. The solid was evaporated twice with 80% ethanol, twice with 80% ethanol containing 2% triethyl amine (TEA), and finally with anhydrous ethanol. There was obtained 44 mg of the bis-triethylamine salt of the title product. A solution of the triethylamine salt in 1 ml methanol was treated with 1 ml of a solution of 6 M NaI in acetone. The precipitate was washed with acetone and dried to give 32 mg of disodium salt of the title product as a white solid.

EXAMPLE 2

Preparation of [$^{32}$S]2',3'-Dideoxyadenosine-5'-(O-1-Thiotriphosphate)

A solution of the bis-triethylamine (TEA) salt of the title product of Example 1 (26 mg, 0.05 mmol) was dissolved in 1 ml dry dioxane and treated with diphenyl phosphochloridate (0.015 ml, 0.075 mmol). The mixture was agitated for 3 hr. at 25° C. A solution of dry pyrophosphate in pyridine was prepared by dissolving the tetrasodium salt (220 mg, 0.5 mmol) in 3 ml pyridine and evaporating twice, and the taking in 0.5 ml pyridine. This solution was added to the above solution of the crude active ester, and stirred for 2 hr. The crude product was precipitated by addition of ether (10 ml). The precipitate was dissolved in water and chromatographed in DEAE-cellulose eluted with 0.1 M triethylammonium bicarbonate. The pooled fractions contained 150 A$_{260}$ units (20%) of the title product. The solution was lypholyzed and the residue stored at −70° C.

EXAMPLE 3

Preparation of [$^{79}$Br]3'-Bromo-2',3'-Deoxythymidine

A solution of 1-(5-O-triphenylmethyl-2'-deoxy-$\beta$-D-threopentofuranosyl)thymine (50 mg, 0.1 mmol) in pyridine (1 ml) was treated with methanesulfonyl chloride (0.014 ml, 0.12 mmol) and the reaction agitated at 10° C. for 6 hr. The mixture was then evaporated, diluted with CHCl$_3$ (5 ml) and washed 2× with water. The organic layer was evaporated, and the crude mesylate dissolved in dry diglyme (1 ml) and treated with [Li$^{79}$Br] (17 mg, 0.2 mmol). The solution was heated for 4 hr. at 100° C., and then diluted with 80% acetic acid (1 ml) and heated 15 min longer. The reaction was cooled and diluted with water (2 ml), and extracted 3× with chloroform (2 ml). The organic extracts were evaporated and the residue chromatographed on silica gel eluted with 95:5 chloroform methanol to give 18 mg of the title product as an off-white solid.

this material could be converted to the triphosphate via the monophosphate as in Example 2. The monophosphate was prepared by reaction with cyanoethyl phosphate and dicyclohexylcarbodiimide (DCC), followed by LiOH deblocking.

EXAMPLE 4

Preparation of [$^{79}$Br]2',3'-Dideoxy-5-Bromocytidine

To a solution of 2',3'-dideoxycytidine (60 mg, 0.3 mmol) in dry DMF (1 ml) was added 0.1 ml pyridine and then [$^{79}$Br] bromine (42 mg, 0.3 mmol), and the mixture agitated for 12 hr. The solvent was evaporated, and the residue chromatographed on silica gel (ethyl acetate:methanol:triethylamine 90:10:1) to give 46 mg of the title product as a white solid.

This material could be converted to the triphosphate via the monophosphate as in Example 2. The monophosphate was prepared by reaction with cyanoethyl phosphate and dicyclohexylcarbodiimide followed by LiOh deblocking.

What is claimed is:

1. In a process for determining DNA sequence by the dideoxynucleotide chain termination method, the improvement comprising incorporating $^{32}$S, $^{33}$S, $^{34}$S and $^{36}$S in the formation of the chain terminated sequence so that a unique sulfur isotope is associated with the terminal nucleotide in the chain terminated sequence, separating the chain terminated sequences by capillary gel electrophoresis, combusting the separated chain terminated sequences to convert the incorporated sulfur to SO$_2$, and determining the terminal nucleotide by measuring $^{64}$SO$_2$, $^{65}$SO$_2$, $^{67}$SO$_2$, and $^{68}$SO$_2$ in a mass spectrometer thereby determining the sequence of the DNA.

2. A process according to claim 1 wherein the isotope is incorporated only into the 2', 3'-dideoxyribonucleotides.

3. A process according to claim 1 wherein the isotope is incorporated only into the 2'-deoxyribonucleotides.

4. A process according to claim 1 wherein the isotope is incorporated into a DNA primer.

* * * * *